US009542587B2

(12) United States Patent
Cheng et al.

(10) Patent No.: US 9,542,587 B2
(45) Date of Patent: Jan. 10, 2017

(54) FINGERPRINT INFORMATION DETECTION CIRCUIT

(71) Applicant: SILEAD, INC., Shanghai (CN)

(72) Inventors: Taiyi Cheng, Shanghai (CN); Xianggui Zhao, Shanghai (CN)

(73) Assignee: Silead, Inc., Shanghai (CN)

( * ) Notice: Subject to any disclaimer, the term of this patent is extended or adjusted under 35 U.S.C. 154(b) by 45 days.

(21) Appl. No.: 14/443,342

(22) PCT Filed: Apr. 29, 2014

(86) PCT No.: PCT/CN2014/076489
§ 371 (c)(1),
(2) Date: May 15, 2015

(87) PCT Pub. No.: WO2015/123921
PCT Pub. Date: Aug. 27, 2015

(65) Prior Publication Data
US 2016/0275331 A1  Sep. 22, 2016

(30) Foreign Application Priority Data
Feb. 20, 2014 (CN) .......................... 2014 1 0058276

(51) Int. Cl.
*G01R 27/08* (2006.01)
*G06K 9/00* (2006.01)
(Continued)

(52) U.S. Cl.
CPC ........... *G06K 9/0002* (2013.01); *G01N 27/228* (2013.01); *H01L 27/0629* (2013.01);
(Continued)

(58) Field of Classification Search
CPC . G06K 9/0002; H01L 27/092; H01L 27/0629; G01N 27/228; H03K 19/00361; H03K 19/00392; G11C 29/785
See application file for complete search history.

(56) References Cited

U.S. PATENT DOCUMENTS 8,618,865 B1    12/2013  Lu
2013/0009665 A1*  1/2013  Clerc ............... H03K 19/00338
                                                  326/28
2015/0177878 A1*  6/2015  Cheng ..................... G06F 3/044
                                                  345/174

FOREIGN PATENT DOCUMENTS

CN    101526990 A    9/2009
CN    203812253 U    9/2014

* cited by examiner

*Primary Examiner* — David Gray
*Assistant Examiner* — Michael Harrison
(74) *Attorney, Agent, or Firm* — Haynes and Boone, LLP

(57) ABSTRACT

The present invention relates to a chip design and discloses a fingerprint information detection circuit. The invention includes a reset unit, a feedback unit, an amplification unit and a source follower unit; the reset unit is connected to the feedback unit and amplification unit, while the feedback unit is connected to the amplification unit, and the amplification unit is connected to the source follower unit; when the reset transistor built-into the reset unit is on, it stores an electric charge, and resets the feedback unit; when the reset transistor is off, the stored electric charge is injected into the feedback unit and amplification unit; the feedback unit receives the electric charge, and outputs the second voltage signal generated when it detects fingerprints to the source follower unit; the amplification unit amplifies the received signal and outputs it to the source follower unit; the source follower unit receives the signal, performs voltage level shifting before outputting the first voltage signal that carries (Continued)

the detected fingerprint information. The present invention enables the circuit to use a reduced chip area, hence, saving the cost of the chip.

20 Claims, 3 Drawing Sheets

(51) Int. Cl.
    *H01L 27/092*     (2006.01)
    *H01L 27/06*     (2006.01)
    *G01N 27/22*     (2006.01)
    *H03K 19/003*     (2006.01)
    *G11C 29/00*     (2006.01)

(52) U.S. Cl.
    CPC .......... *H01L 27/092* (2013.01); *G11C 29/785* (2013.01); *H03K 19/00361* (2013.01); *H03K 19/00392* (2013.01)

FINGERPRINT INFORMATION DETECTION CIRCUIT

CROSS-REFERENCE TO RELATED APPLICATIONS

This application is a United States national phase application of co-pending Patent Cooperation Treaty Application No. PCT/CN2014/076489, filed Apr. 29, 2014, which claims priority to Chinese Application No. CN2014100582765 filed Feb. 20, 2014, the disclosures of which are incorporated herein by reference.

TECHNICAL FIELD

The present invention relates to a chip design, particularly to a fingerprint information detection circuit.

BACKGROUND

Biometrics that is used to authenticate and identify personal information is usually realized through physical characteristics (e.g., hair, fingerprints, blood, etc.). When choosing physical characteristics, considerations are given to different aspects, such as the cost of production, ease of processing, reliability, comfort, and so on. Fingerprint is the most reliable feature in biometrics. It is uniquely special, yet in the personal consumer market, application of fingerprints is not very mature because it is affected by production design on the one hand, and restricted by cost factors on the other hand.

So far the principle employed by the fingerprint sensor device mainly involves optics, integrated pressure, capacitance, and the like. The main reason for the disadvantage of the optical imaging fingerprint identification unit is that it creates a relatively large volume and requires a clean surface; the major restriction for integrated pressure sensing unit is the supper high cost because it is not commonly used; and fingerprint information detection circuit based on capacitive sensing unit may avoid the disadvantages of the first two methods, with its general circuit configuration shown in FIG. 1, comprising a signal input unit, a reset unit, an amplification unit, a feedback unit and a source follower unit.

In FIG. 1, 101 is a signal input unit, 102 is a reset unit, 103 the amplification unit, 104 the feedback unit and 105 the source follower unit.

However, the above-described circuit takes up a huge chip area, increasing the cost on chips.

In addition, the clock feedthrough effect and the electric charge injection effect generated by the reset unit affect the voltage signal outputted by the circuit, namely affecting the results of fingerprint detection.

INVENTION SUMMARY

The objective of the present invention is to provide a fingerprint information detection circuit to improve the utilization of the reset transistor so that the circuit does not take up that much chip area, hence saving the cost on the chip, while at the same time purifying the source electric charge.

To solve the above technical problem, the present invention provides a fingerprint information detection circuit that comprises an amplification unit and a source follower unit; the amplification unit is coupled to the source follower unit; the amplification unit receives and amplifies a signal, then outputs it to the source follower unit; the source follower unit receives the signal, and performs voltage level shifting before outputting a first voltage signal, wherein the first voltage signal carries the detected fingerprint information. The fingerprint information detection circuit further comprises a reset unit and a feedback unit.

The feedback unit outputs a second voltage signal when detecting fingerprint information to the source follower unit.

The reset unit is coupled to the feedback unit and the amplification unit; the feedback unit is coupled to the amplification unit; an input port of the reset unit is used for inputting a reset signal.

When the reset signal is of a high level, the reset transistor inside the reset unit is on and stores the electric charge, while resetting the feedback unit; when the reset signal is switched from the high level to a low level, the reset transistor is off, and the electric charge stored is injected to the feedback unit and the amplification unit.

The feedback unit receives the electric charge, and outputs the second voltage signal to the source follower unit when detecting fingerprint information.

In comparison to the prior art, the embodiments of the invention utilize a built-in reset transistor in the reset unit to generate the injected electric charge, which eliminates the need for an additional input unit for generating injected electric charge. More specifically, the fingerprint information detection circuit in the present invention includes an amplification unit, a source follower unit, a reset unit, and a feedback unit; the reset unit is coupled to the feedback unit and the amplification unit, while the feedback unit is coupled to the amplification unit, and the amplification unit is coupled to the source follower unit, and the input port of the reset unit is used for inputting the reset signal; wherein the feedback unit outputs the second voltage signal generated upon detection of fingerprint information to the source follower unit, the amplification unit receives and amplifies the signal before outputting it to the source follower unit; then the source follower unit receives the signal, performs voltage level shifting before outputting a first voltage signal, the first voltage signal carries fingerprint information detected. The key is that when the reset signal is high, the reset transistor built-into the reset unit is on and stores electric charge, that is, when the reset transistor is on, there is no electric charge stored in the feedback unit, namely the reset transistor resets the feedback unit; while the reset transistor is on, it forms a plate capacitor to store electric charge; when the reset signal is switched from high to low, the reset transistor is off and injects stored electric charge to the feedback unit and amplification unit; the feedback unit receives an electric charge as the original electric charge it stores, while generating an original third voltage signal, and outputs second voltage signal generated upon detection of fingerprint information to the source follower unit. The present invention utilizes the injection of electric charge into the feedback unit when the reset transistor is off, instead of adding an additional input unit to generate the electric charge for being injected into the feedback unit, thereby improving utilization of the reset transistor, reducing the area of chip occupied by the fingerprint information detection circuit, and saving on cost of the chip. In addition, the reset unit may be placed beneath the feedback unit in the chip, which further reduces the area of chip used by the fingerprint information detection circuit, thereby saving more on the cost of the chip. Meanwhile, all of the electric charge injected into the feedback unit is from the electric charge stored in the reset transistor, which purifies the source of electric charge injected to the feedback unit.

Furthermore, the reset unit is comprised of a first inverter, a second inverter, a third inverter, and a first N-channel metal-oxide-semiconductor field effect transistor (NMOSFET).

An input port of the first inverter is the input port of the reset unit, and an output port of the first inverter is coupled to an input port of the second inverter;

An output port of the second inverter is coupled to an input port of the third inverter.

An output port of the third inverter is coupled to a gate electrode of the first NMOSFET.

A source electrode and a drain electrode of the first NMOSFET are coupled, wherein the drain electrode is a first output port of the reset unit;

A first port of the reset transistor and the first output port of the reset unit are coupled, while a second port of the reset transistor is a second output port of the reset unit, and a third port is coupled to the output port of the second inverter.

The reset transistor is a second NMOSFET;

A source electrode of the second NMOSFET is the first port of the reset transistor; a drain electrode of the second NMOSFET is the second port of the reset transistor; a gate electrode of the second NMOSFET is the third port of the reset transistor.

The channel width of the reset transistor is twice the channel width of the first NMOSFET.

Based on the above connections, when inputting the reset signal, the reset transistor produces a clock feedthrough effect, which generates an electric charge that can be calculated by using the following equation:

$$Q_{clk1} = V_{clk1} W_1 C_{ov},$$

Wherein $V_{clk1}$ is the clock voltage of the reset transistor, $W_1$ is the channel width of the reset transistor, and $C_{ov}$ is the overlap capacitance per unit width.

Meanwhile, the first NMOSFET absorbs the reset transistor's electric charge generated due to clock feedthrough. The electric charge generated due to clock feedthrough that is absorbed by the first NMOSFET is calculated by the following equation:

$$Q_{clk2} = V_{clk2} 2 W_2 C_{ov},$$

Wherein, $V_{clk2}$ is the clock voltage for the first NMOSFET, and obtained when $V_{clk1}$ goes through the third inverter; both have opposite phases; $W_2$ is the channel width of the first NMOSFET, while $C_{ov}$ is the overlap capacitance per unit width.

Since the channel width of the reset transistor is twice the channel width of the first NMOSFET, i.e. $W_1 = 2W_2$, the electric charge generated by clock feedthrough for the reset transistor is fully absorbed by the first NMOSFET due to clock feedthrough. Hence, the electric charge generated by clock feedthrough is eliminated, so that the electric charge injected into the feedback unit is all from the electric charge stored in the reset transistor, which purifies the source of electric charge injected into the feedback unit.

Further, the feedback unit is grounded. Thus, upon touch of the finger, the static electricity on the finger is discharged to the ground, protecting the reset unit, the amplification unit and the source follower unit coupled to the feedback unit from electrostatic breakdown caused by the static electricity on the finger.

Further, the feedback unit comprises a first capacitor, a second capacitor, and a third capacitor.

A positive electrode of the first capacitor is coupled to a first port of the feedback unit, while a negative electrode of the first capacitor is coupled to a second port of the feedback unit.

The first port of the feedback unit is coupled to the first output port of the reset unit, while the second port of the feedback unit is coupled to the second output port of the reset unit.

A positive electrode of the second capacitor is coupled to the first port of the feedback unit, while a negative electrode of the second capacitor is grounded.

A positive electrode of the third capacitor is coupled to the second port of the feedback unit, while a negative electrode of the third capacitor is grounded.

This is the composition of the feedback unit without finger touch. When there is finger touch, the feedback unit further includes a fourth capacitor, a fifth capacitor, a sixth capacitor, and a resistor.

A positive electrode of the fourth capacitor is coupled to the first port of the feedback unit, while a negative electrode of the fourth capacitor is coupled to a positive electrode of the fifth capacitor.

A negative electrode of the fifth capacitor is coupled to the second port of the feedback unit.

A positive electrode of the sixth capacitor is coupled to the negative electrode of the fourth capacitor, while a negative electrode of the sixth capacitor is grounded.

One terminal of the resistor is coupled to the positive electrode of the fifth capacitor, while the other terminal is grounded.

Thus, the distances from the first capacitor and the fingerprint to the feedback unit are non-linear. Hence, the second voltage signal generated by the feedback unit due to detection of fingerprint information can accurately represent the distance between the fingerprint and the feedback unit, and ultimately the first voltage signal outputted by the fingerprint information detection circuit can more accurately reflect the distance from the fingerprint to the feedback unit.

DETAILED DESCRIPTION

Figure 1:
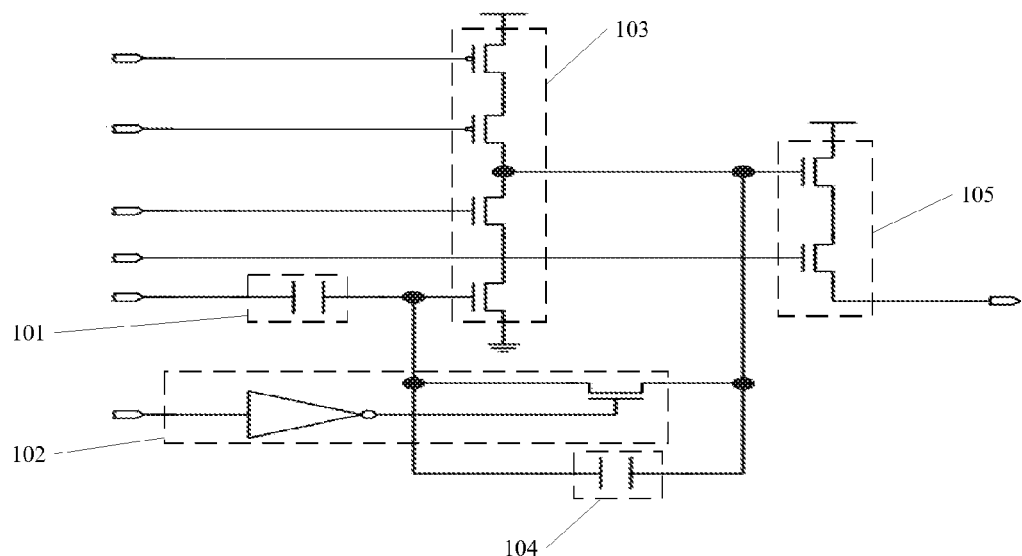
FIG. 1 is a schematic diagram for the fingerprint information detection circuit based on the prior art.

To make the objectives, technical solutions and advantages of the present invention more apparent, detailed descriptions are provided below in conjunction with the drawing for each embodiment of the present invention. However, person having ordinary skill in the art should appreciate that each embodiment of the present invention provides technical details only to facilitate readers to have a better understanding of the present disclosure. Even without such technical details or various alterations and modifications based on the following embodiments, technical solutions within the scope of the present disclosure as provided by the claims can still be realized.

Figure 2:
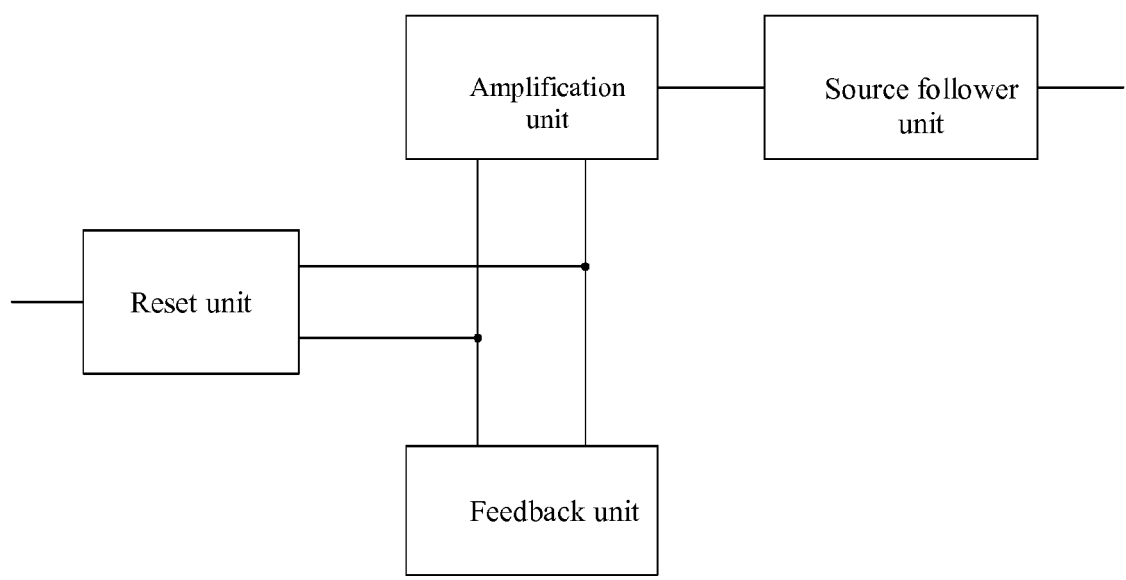
FIG. 2 is a schematic view of the fingerprint information detection circuit based on the first embodiment of the present invention.

The first embodiment of the present invention relates to a fingerprint information detection circuit with the specific configuration shown in FIG. 2, which comprises a reset unit, an amplification unit, a feedback unit, and a source follower unit.

The feedback unit outputs the second voltage signal generated upon detection of fingerprint information to the source follower unit.

As shown in FIG. 2, the reset unit is coupled to the feedback unit and the amplification unit; the feedback unit is coupled to the amplification unit; the amplification unit is coupled to the source follower unit; and the input of the reset unit is used for inputting the reset signal.

When the reset signal is high, the reset transistor built-into the reset unit is on and stores electric charge, while resetting the feedback unit. Specifically, when the reset transistor is on, the feedback unit has no stored electric charge, i.e., the reset transistor resets the feedback unit, and clears the electric charge stored in the feedback unit; at the same time, the reset transistor forms a plate capacitor when it is on to store the electric charge.

When the reset signal is switched from high to low, the reset transistor is off, and injects the stored electric charge to the feedback unit and the amplification unit.

The feedback unit receives the electric charge, and outputs the second voltage signal generated when the fingerprint information is detected to the source follower unit. Specifically, the feedback unit receives the electric charge injected from the reset transistor as the original electric charge stored in the feedback unit, and produces the original third voltage signal, which is the voltage signal generated when no fingerprint is detected; the feedback unit outputs the second voltage signal generated when fingerprint information is detected to the source follower unit.

The source follower unit receives the signal and performs voltage level shifting on it before outputting the first voltage signal, which carries the fingerprint information detected.

Further, the amplification unit amplifies the received signal and outputs it to the source follower unit. More specifically, when the amplification unit receives the electric charge, the input voltage signal is changed. The amplification unit amplifies the changed input voltage signal and then outputs it to the source follower unit. Moreover, the amplified output voltage signal and the second voltage signal are the same.

Compared with the prior art, this embodiment not only utilizes the reset transistor in the feedback unit to reset the feedback unit, but also employs the reset transistor to generate injected electric charge, without the need to add a separate input unit to generate the injected electric charge, thus improving the utilization of the reset transistor, reducing the area of chip occupied by the fingerprint information detection circuit, and saving on the cost of the chip. Furthermore, the reset unit may be placed beneath the feedback unit in the chip, which further reduces the area of chip used by the fingerprint information detection circuit, thereby saving more on the cost of the chip. Meanwhile, all of the electric charge injected into the feedback unit is from the electric charge stored in the reset transistor, which purifies the source of electric charge injected to the feedback unit.

It is worth mentioning that each module involved in the present embodiment is a logic module; in practical applications, a logic unit may be a physical unit, or part of a physical unit, or combination of multiple physical units. In addition, in order to highlight the innovative part of the present invention, the present embodiment does not introduce units that are not closely related to the technical problem proposed to be resolved by the invention, which does not indicate that no other units exist in the present embodiment.

The second embodiment of the present invention relates to a fingerprint information detection circuit. The second embodiment made further refinement on the basis of the first embodiment and provides a specific circuit structure for the reset unit, the feedback unit, the amplification unit and the source follower unit, as shown in FIG. 3 and FIG. 4.

Figure 3:
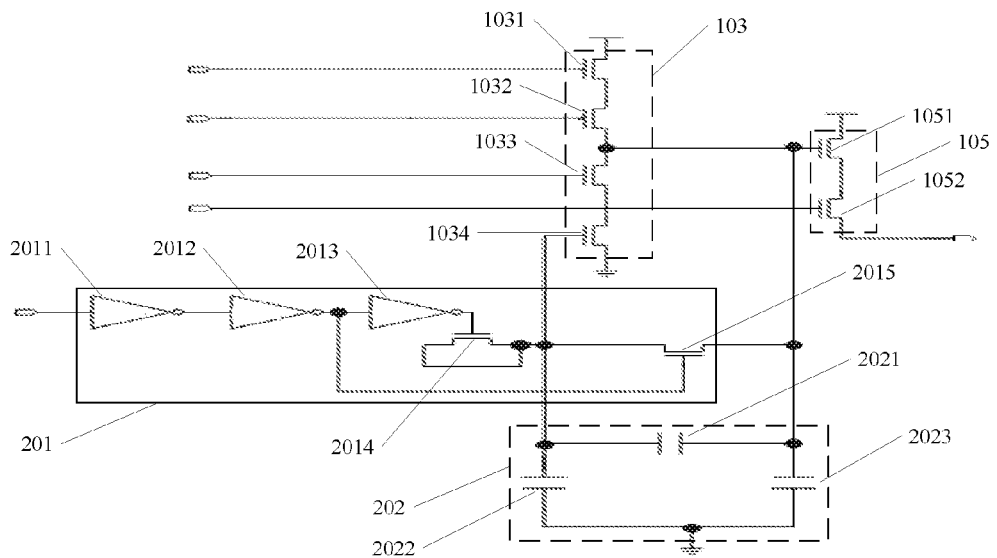
FIG. 3 is a schematic diagram of the fingerprint information detection circuit based on the second embodiment of the present invention when no fingerprint information is detected.
Figure 4:
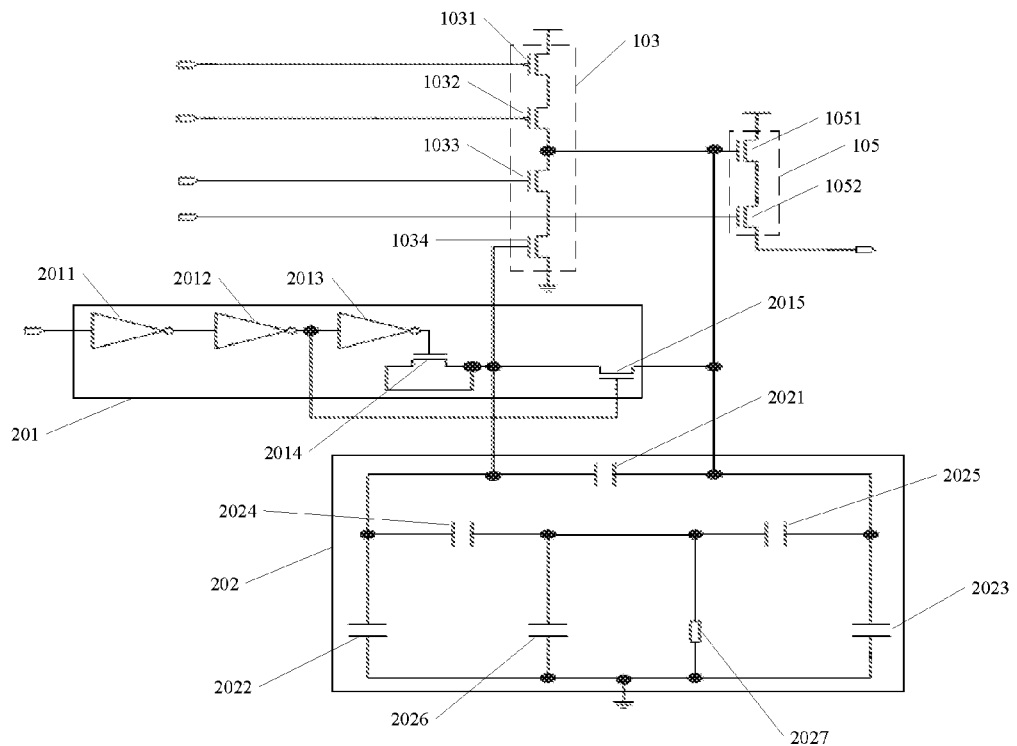
FIG. 4 is a schematic diagram of the fingerprint information detection circuit based on the second embodiment of the present invention when fingerprint information is detected.

Wherein, FIG. 3 is a schematic view of the fingerprint information detection circuit when no fingerprint information is detected, FIG. 4 is a schematic view of the fingerprint information detection circuit when fingerprint information is detected. The difference between FIG. 3 and FIG. 4 is only the change to the feedback unit when it detects the fingerprint information.

In FIG. 3 and FIG. 4, 201 is the reset unit, 2011 the first inverter, 2012 the second inverter, 2013 the third inverter, and 2014 the first N-channel metal-oxide-semiconductor field effect transistor (NMOSFET); 202 is the feedback unit, 2021 the first capacitor, 2022 the second capacitor, 2013 the third capacitor ; 103 is the amplification unit, 1031 is the first P-channel metal-oxide-semiconductor field effect transistor (PMOSFET), 1032 the second PMOSFET, 1033 the third NMOSFET, 1034 the fourth NMOSFET; 105 is a source follower unit, 1051 the source follower, and 1052 is the switch.

In FIG. 4, 2024 is the fourth capacitor, 2025 the fifth capacitor, 2026 the sixth capacitor, and 2027 the resistor.

Firstly, the specific structure of the reset unit is described. In addition to having a reset transistor, the reset unit further comprises a first inverter, a second inverter, a third inverter and the first NMOSFET.

The input port of the first inverter is the input port of the reset unit, while its output port is coupled to the input port of the second inverter; the output port of the second inverter is coupled to the input port of the third inverter; the output port of the third invertor is coupled to the gate electrode of the first NMOSFET; the source electrode and drain electrode of the first NMOSFET are connected, wherein the drain electrode is the first output port of the reset unit; the first port of the reset transistor is coupled to the first output port of the reset unit, and its second port is the second output port for the reset unit, while the third port is coupled to the output port of the second inverter.

The reset transistor is the second NMOSFET; the source electrode of the second NMOSFET is the first port of the reset transistor; the drain electrode of the second NMOSFET is the second port of the reset transistor; the gate electrode of the second NMOSFET is the third port of the reset transistor.

Moreover, the channel width of the reset transistor is twice the channel width of the first NMOSFET.

Based on the above connections, when inputting the reset signal, the reset transistor produces the clock feedthrough effect, which generates an electric charge that can be calculated by using the following equation:

$$Q_{clk1} = V_{clk1} W_1 C_{ov},$$

Wherein $V_{clk1}$ is the clock voltage of the reset transistor, $W_1$ is the channel width of the reset transistor and $C_{ov}$ is the overlap capacitance per unit width.

Meanwhile, the first NMOSFET absorbs the reset transistor's electric charge generated due to clock feedthrough. The electric charge absorbed by the first NMOSFET due to clock feedthrough is calculated by the following equation:

$$Q_{clk2}=V_{clk2}2W_2C_{ov},$$

Wherein, $V_{clk2}$ is the clock voltage for the first NMOSFET, and obtained when $V_{clk1}$ goes through the third inverter; both have opposite phases, namely $V_{clk2}=-V_{clk1}$; $W_2$ is the channel width of the first NMOSFET, while $C_{ov}$ is the overlap capacitance per unit width.

Since the channel width of the reset transistor is twice the channel width of the first NMOSFET, i.e. $W_1=2W_2$, so $$Q_{clk1}+Q_{clk2}=0,$$

Namely, the electric charge generated by clock feedthrough for the reset transistor is fully absorbed by the first NMOSFET due to clock feedthrough. Hence, the electric charge generated by clock feedthrough is eliminated, so that the electric charge injected into the feedback unit is all from the electric charge stored in the reset transistor, which purifies the source of electric charge injected into the feedback unit.

It is worth mentioning that the reset transistor generates a clock feedthrough effect when it is off, and generates an electric charge injection effect when it is on. In the prior art, both of them adversely affect the circuit, whereas in the present embodiment, the electric charge produced from the electric charge injection effect is utilized and injected into the amplification unit and the feedback unit. To purify the electric charge injected into the amplification unit and the feedback unit, the first NMOSFET is used to fully absorb all of the electric charge generated due to the clock feedthrough in the reset transistor. This not only reduces the design workload for adding an input unit for generating the electric charge as well as reduces the area of the chip used by the fingerprint information detection circuit chip, but also eliminates the adverse effects of the electric charge generated by the clock feedthrough effect.

Note that the reset transistor forms a plate capacitor when it is on, and the total electric charge stored is $$Q_1=W_1L_{eff1}C_{OX}(V_{DD}-V_{i1}-V_{t1}),$$

Wherein, $W_1$ is the channel width of the reset transistor, $L_{eff1}$ is the effective channel width of the reset transistor, $C_{OX}$ is the gate electrode oxide thickness of the reset transistor, $V_{DD}$ is the first operating voltage, while $V_{i1}$ is the DC input level established by the fourth NMOSFET and $V_{t1}$ is the turn-on threshold voltage of the reset transistor.

When the reset transistor is off, the electric charge $Q_1$ stored in the reset transistor when it is on flows out through the first and second port, namely through the source electrode and the drain electrode of the second NMOSFET, with half of the total electric charge through each path. At the same time, the first NMOSFET is on and absorbs some of the electric charge generated by the reset transistor, and the absorbed electric charge amount is $$Q_2=W_2L_{eff2}C_{OX}(V_{DD}-V_{i2}-V_{t2}),$$

Wherein, $W_2$ is the channel width of the first NMOSFET, $L_{eff2}$ is the effective channel width of the first NMOSFET, $C_{OX}$ is the gate electrode oxide thickness of the first NMOSFET, $V_{DD}$ is the first operating voltage, $V_{i2}$ is the DC input level established by the fourth NMOSFET when the reset transistor is off, and $V_{t2}$ is the turn-on threshold voltage for the first NMOSFET.

What is worth mentioning is that the first inverter, the second inverter and the third inverter are used to shape the received signal. The shorter the third inverter's delay or the transition time, the higher the electric charge absorbed by the first NMOSFET; at the same time, the shorter the second inverter's delay or the transition time, the more the total amount of electric charge generated in the reset transistor.

Thus, the injection electric charge generated in the reset transistor and injected into the amplification unit and the feedback unit is $$Q_3=Q_1/2-Q_2,$$

That is, the electric charge injected into the amplification unit and the feedback unit is the injection electric charge from the reset transistor; hence, the electric charge source is pure.

Below, specific structure of the feedback unit is introduced. In the present embodiment, the feedback unit is grounded. Thus, when the finger touches it, the static electricity on the finger is discharged to the ground, protecting the reset unit, the amplification unit and the source follower unit coupled to the feedback unit from electrostatic breakdown caused by the static electricity on the finger.

When fingerprint information is not detected, fingerprint information detection circuit diagram is shown in FIG. 3, and the feedback unit comprises a first capacitor, a second capacitor and a third capacitor.

The positive electrode of the first capacitor is coupled to the first port of the feedback unit, while its negative electrode is coupled to the second port of the feedback unit; wherein, the first port of the feedback unit is coupled to the first output port of the reset unit, while its second port is coupled to the second output port of the reset unit. The positive electrode of the second capacitor is coupled to the first port of the feedback unit, while its negative electrode is grounded; the positive electrode of the third capacitor is coupled to the second port of the feedback unit, while its negative electrode is grounded.

Figure 5:
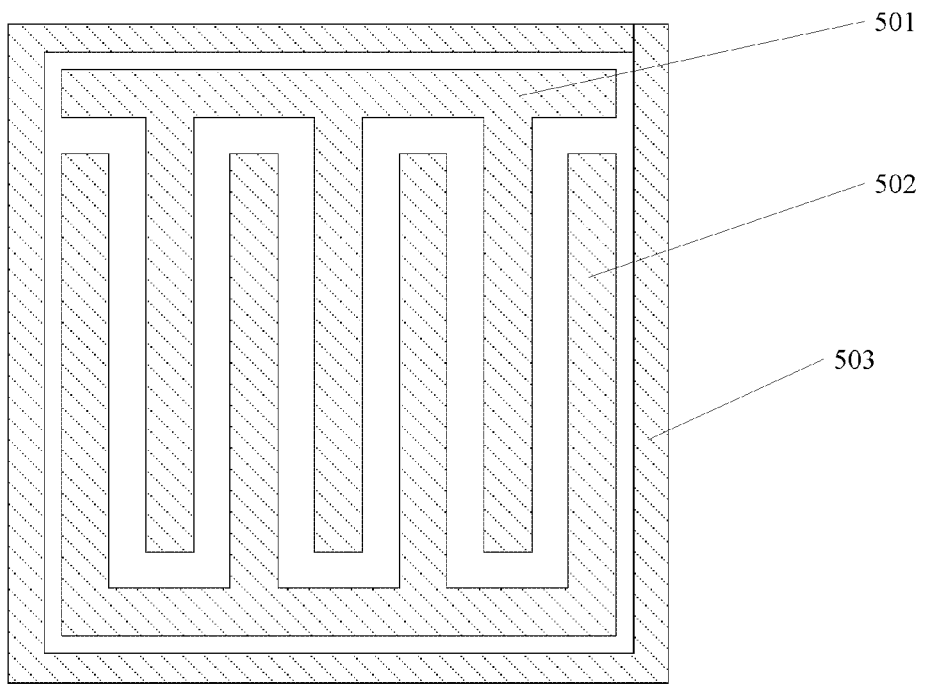
FIG. 5 is the top view of the first structure for the inner plate, the outer plate, and the ground loop based on the second embodiment of the present invention.
Figure 6:
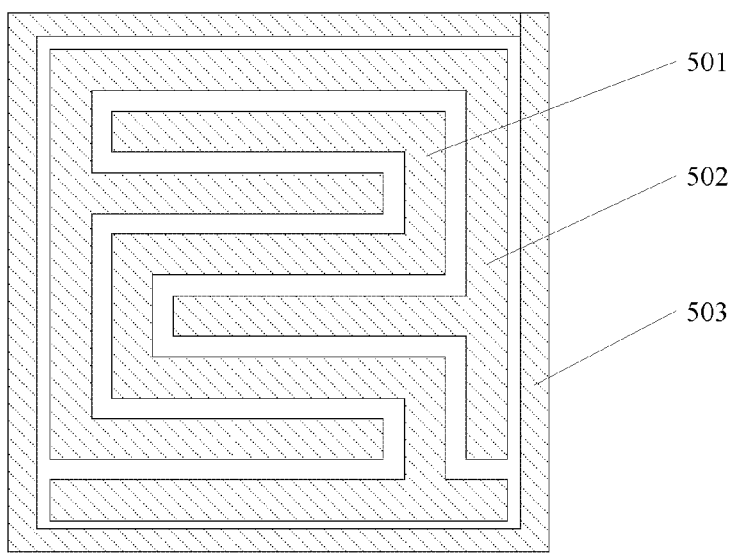
FIG. 6 is the top view of the second structure for the inner plate, the outer plate, and the ground loop based on the second embodiment of the present invention.

In the above, the first capacitor is the coupling capacitor between the feedback unit's outer plate and inner plate, the second capacitor is the coupling capacitor between the outer plate and the ground loop, and the third capacitor is the coupling capacitor between the inner plate and the ground loop. The structure of the inner plate, outer plate and the ground loop can be designed as needed. FIG. 5 shows a top view of a first structure for the inner plate, outer plate and the ground loop, and FIG. 6 shows a top view of a second structure. The present embodiment preferably chooses the structure of the inner plate, outer plate and the ground loop represented in FIG. 5, which enables the feedback unit to be more sensitive to the distance from the fingerprint ridges and valleys to the plate of the first capacitor built into the feedback unit, hence, better electrostatic protection.

In FIG. 5 and FIG. 6, 501 is the inner plate, 502 is the outer plate and 503 is the ground loop.

When fingerprint information is detected, the fingerprint information detection circuit is shown in FIG. 4 where the feedback unit further includes a fourth capacitor, a fifth capacitor, a sixth capacitor and a resistor.

In FIG. 4, the positive electrode of the fourth capacitor is coupled to the first port of the feedback unit, while its negative electrode is coupled to the positive electrode of the fifth capacitor; the negative electrode of the fifth capacitor is coupled to the second port of the feedback unit; the positive electrode of the sixth capacitor is coupled to the negative electrode of the fourth capacitor, while its negative electrode is grounded; one terminal of the resistor is coupled to the positive electrode of the fifth capacitor, and the other terminal is grounded.

In the above, the fourth capacitor is the coupling capacitance between the outer plate of the feedback unit and the finger, the fifth capacitor is the coupling capacitance between the inner plate and the finger, the sixth capacitor is the coupling capacitance between the ground loop and the finger, while the resistor is the resistance between the human body and the ground loop.

When the feedback unit detects fingerprint information, the capacitance value of the feedback unit's first capacitor is changed, so that the voltage signal generated by the first capacitor is changed from the third voltage signal when no fingerprint information is detected to the second voltage signal, which carries the detected fingerprint information.

In the present embodiment, the distances from the first capacitor and the fingerprint to the feedback unit are non-linear; hence, the second voltage signal generated by the feedback unit due to detection of fingerprint information can accurately represent the distance between the fingerprint and the feedback unit, and ultimately the first voltage signal outputted by the fingerprint information detection circuit can more accurately reflect the distance from the fingerprint to the feedback unit.

Next, the structure of the amplification unit is described. As shown in FIGS. 3 and 4, the amplification unit comprises: a first PMOSFET, a second PMOSFET, a third NMOSFET and a fourth NMOSFET.

In FIGS. 3 and 4, the gate electrode of the first PMOSFET is the first port of the amplification unit for inputting the first bias voltage, and its source electrode is the second port of the amplification unit for inputting the first operating voltage, while its drain electrode is coupled to the source electrode of the second PMOSFET; the gate electrode of the second PMOSFET is the third port of the amplification unit for inputting the second bias voltage, and its drain electrode is the fourth port of the amplification unit, and coupled to the drain electrode of the third NMOSFET; the gate electrode of the third NMOSFET is the fifth port of the amplification unit for inputting the third bias voltage, and its source electrode is coupled to the drain electrode of the fourth PMOSFET; the gate electrode of the fourth PMOSFET is the sixth port of the amplification unit and is coupled to the first output port of the reset unit, while its source electrode is grounded.

The amplification unit amplifies the received signal and then outputs it. Since the amplification unit is known in the art, it is not repeated here.

Last but not least, the structure of the source follower is described. The source follower unit comprises a source follower and a switch; the source follower is coupled to the switch.

Further, the source follower is the fifth NMOSFET; and the switch is the sixth NMOSFET; the drain electrode of the fifth NMOSFET is the first port of the source follower unit for inputting the second operating voltage, and its gate electrode is the second port of the source follower unit and is coupled to the fourth port of the amplification unit, its source electrode is coupled to the drain electrode of the sixth NMOSFET; the gate electrode of the sixth NMOSFET is the third port of the source follower for inputting a switch signal, and its source electrode is the fourth port of the source follower for outputting the first voltage signal, which carries the fingerprint information detected.

The source follower unit receives the signal, performs voltage level shifting and then outputs the first voltage signal. Since the source follower unit is known in the art, it is not repeated here.

So far, the structure of the fingerprint information detection circuit has been described in embodiments.

It is worth mentioning the relationship between the injected electric charge, the first capacitance built into the feedback unit and fingerprint information. It is described as follows:

The amount of electric charge injected into the amplification unit and the feedback unit by the reset transistor are, $Q_4$ and $Q_5$ respectively, thus:

$$Q_3 = Q_4 + Q_5,$$

Moreover, the electric charge injected into the amplification unit is actually the electric charge injected into the fourth NMOSFET; therefore, $$Q_4 = C_{in1} \Delta V_{in1},$$

Wherein, $C_{in1}$ is the capacitance value of the fourth NMOSFET, $\Delta V_{in1}$ is the amount of change in the input voltage generated by the electric charge injection, and $$C_{in1} = W_3 L_{eff3} C_{OX},$$

Wherein, $W_3$ is the channel width of the fourth NMOSFET, $L_{eff3}$ is the effective channel width of the fourth NMOSFET, and $C_{OX}$ is the gate electrode oxide thickness.

Similarly, the electric charge injected into the feedback unit is actually the electric charge injected into the first capacitor; therefore, $$Q_5 = C_1 \Delta V_2,$$

Wherein, $C_1$ is the capacitance value of the first capacitance, $\Delta V_2$ is the amount of change to the voltage generated on both ends of the first capacitor due to electric charge injection.

Also, because of $$\Delta V_2 = \Delta V_{O1} - \Delta V_{in1},$$

$$\Delta V_{O1} = A_{v0} \Delta V_{in1},$$

Wherein, $\Delta V_{O1}$ is $\Delta V_{in1}$ after being amplified by the amplification unit.

Upon simplification, and in conjunction with the condition that $A_{v0} \gg 1$, it can be derived that:

$$\Delta V_{O1} = \frac{Q_3}{C_1},$$

Wherein, $\Delta V_{O1}$ is the same as the second voltage signal; $\Delta V_{O1}$ then goes through the source follower unit for voltage level shifting and obtains the first voltage signal, which carries the fingerprint information.

From the above equation, it can be seen that the change to the capacitance value of the first capacitor determines the change to the first voltage signal outputted, while the change to the first capacitance value is determined by the fingerprint information detected. Therefore, the detected fingerprint information ultimately determines the first voltage signal outputted, i.e., the first voltage signal carries the fingerprint information as voltage signal. The fingerprint information contains the distance of the fingerprint ridges and valleys to the plate of the first capacitor. That is, when the first capacitor has the electric charge stored, the capacitance value of the first capacitance is changed when the fingerprint information is detected, causing a change to the outputted first voltage signal; therefore, the first voltage signal carries the detected fingerprint information.

Person having ordinary skill in the art should appreciate that the above-described embodiments are examples for carrying out the present invention. In practical applications, they may make various changes to the form and details therein, without departing from the spirit and scope of the present invention.

The invention claimed is:

1. A fingerprint information detection circuit, comprising:
an amplification unit;
a source follower unit;
a reset unit; and
a feedback unit, wherein:
the amplification unit is coupled to the source follower unit;
the amplification unit is configured to receive a signal, amplify the signal to be an amplified signal, and output the amplified signal to the source follower unit;
the source follower unit is configured to receive the amplified signal, perform voltage level shifting, and output a first voltage signal; wherein the first voltage signal carries fingerprint information;
the reset unit is coupled to both the feedback unit and the amplification unit;
the feedback unit and the amplification unit are coupled;
an input port of the reset unit is used for inputting a reset signal;
when the reset signal is of a high level, a reset transistor inside the reset unit becomes open, stores electric charge, and resets the feedback unit; when the reset signal is switched from the high level to a low level, the reset transistor is turned off, and injects the stored electric charge into the feedback unit and the amplification unit; and
the feedback unit is configured to receive the electric charge, and output a second voltage signal to the source follower unit when it detects the fingerprint information.

2. The fingerprint information detection circuit of claim 1, wherein:
the reset unit comprises a first inverter, a second inverter, a third inverter, and a first N-channel metal-oxide-semiconductor field effect transistor (NMOSFET);
an input port of the first inverter is the input port of the reset unit, and an output port of the first inverter is coupled to an input port of the second inverter;
an output port of the second inverter is coupled to an input port of the third inverter;
an output port of the third inverter is coupled to a gate electrode of the first NMOSFET;
a source electrode and a drain electrode of the first NMOSFET are coupled, wherein the drain electrode is a first output port of the reset unit; and
a first port of the reset transistor and the first output port of the reset unit are coupled, a second port of the reset transistor is a second output port of the reset unit, and a third port of the reset transistor is coupled to the output port of the second inverter.

3. The fingerprint information detection circuit of claim 2, wherein the reset transistor is a second NMOSFET; and
wherein a source electrode of the second NMOSFET is the first port of the reset transistor, a drain electrode of the second NMOSFET is the second port of the reset transistor; a gate electrode of the second NMOSFET is the third port of the reset transistor.

4. The fingerprint information detection circuit of claim 3, wherein a channel width of the reset transistor is twice a channel width of the first NMOSFET.

5. The fingerprint information detection circuit of claim 2, wherein the feedback unit is grounded.

6. The fingerprint information detection circuit of claim 5, wherein the feedback unit comprises a first capacitor, a second capacitor, and a third capacitor, wherein:
a positive electrode of the first capacitor is coupled to a first port of the feedback unit, while a negative electrode of the first capacitor is coupled to a second port of the feedback unit;
the first port of the feedback unit is coupled to the first output port of the reset unit, while the second port of the feedback unit is coupled to the second output port of the reset unit;
a positive electrode of the second capacitor is coupled to the first port of the feedback unit, while a negative electrode of the second capacitor is grounded; and
a positive electrode of the third capacitor is coupled to the second port of the feedback unit, while a negative electrode of the third capacitor is grounded.

7. The fingerprint information detection circuit of claim 6 wherein the feedback unit further comprises a fourth capacitor, a fifth capacitor, a sixth capacitor, and a resistor, wherein:
a positive electrode of the fourth capacitor is coupled to the first port of the feedback unit, while a negative electrode of the fourth capacitor is coupled to a positive electrode of the fifth capacitor;
a negative electrode of the fifth capacitor is coupled to the second port of the feedback unit;
a positive electrode of the sixth capacitor is coupled to the negative electrode of the fourth capacitor, while a negative electrode of the sixth capacitor is grounded; and
one terminal of the resistor is coupled to the positive electrode of the fifth capacitor, while the other terminal of the resistor is grounded.

8. The fingerprint information detection circuit of claim 1 wherein:
the amplification unit comprises a first P-channel metal-oxide-semiconductor field effect transistor (PMOSFET), a second PMOSFET, a third NMOSFET and a fourth NMOSFET;
a gate electrode of the first PMOSFET is a first port of the amplification unit that is used for inputting a first bias voltage, a source electrode of the first PMOSFET is a second port of the amplification unit that is used for inputting a first work voltage, and a drain electrode of the first PMOSFET is coupled to a source electrode of the second PMOSFET;
a gate electrode of the second PMOSFET is a third port of the amplification unit to be used for inputting a second bias voltage, a drain electrode of the second PMOSFET is a fourth port of the amplification unit, and is coupled to a drain electrode of the third NMOSFET;
a gate electrode of the third NMOSFET is a fifth port of the amplification unit to be used for inputting a third bias voltage, while a source electrode of the third NMOSFET is coupled to a drain electrode of the fourth NMOSFET; and
a gate electrode of the fourth NMOSFET is a sixth port of the amplification unit and is coupled to the first output of the reset unit, and a source electrode of the fourth NMOSFET is grounded.

9. The fingerprint information detection circuit of claim 8 wherein the source follower unit comprises a source follower and a switch; and the source follower is coupled to the switch.

10. The fingerprint information detection circuit of claim 9 wherein:

the source follower is a fifth NMOSFET;
the switch is a sixth NMOSFET;
a drain electrode of the fifth NMOSFET is a first port of the source follower unit and is to be used for inputting a second operating voltage, a gate electrode of the fifth NMOSFET is a second port of the source follower unit and is coupled to the fourth port of the amplification unit, while a source electrode of the fifth NMOSFET is coupled to a drain electrode of the sixth NMOSFET; and
a gate electrode of the sixth NMOSFET is a third port of the source follower unit and is to be used for inputting a switch signal, while a source electrode of the sixth NMOSFET is a fourth port of the source follower and is to be used for outputting the first voltage signal.

11. A fingerprint information detection circuit, comprising:

an amplification unit;
a source follower unit;
a reset unit; and
a feedback unit, wherein:
the amplification unit is coupled to the source follower unit;
the reset unit is coupled to both the feedback unit and the amplification unit;
the feedback unit and the amplification unit are coupled;
the reset unit includes a reset transistor that is configured to store electric charges when it is turned on, and to inject stored electric charges into the feedback unit and the amplification unit when it is turned off;
the reset unit further includes a second transistor that is configured to absorb electric charges that are generated by the reset transistor due to clock feedthrough;
the feedback unit includes a first capacitor that is configured to receive a portion of the stored electric charges;
the feedback unit is configured to effectuate a change of capacitance when fingerprint information is detected; and
the amplification unit and the source follower unit are configured to output a voltage signal in relation to the change of capacitance in the feedback unit.

12. The fingerprint information detection circuit of claim 11, wherein:

the reset transistor is a NMOSFET;
the second transistor is another NMOSFET; and
a channel width of the reset transistor is twice a channel width of the second transistor.

13. The fingerprint information detection circuit of claim 12, wherein:

the reset unit further includes a first inverter whose input is coupled to a gate electrode of the reset transistor and whose output is coupled to a gate electrode of the second transistor;
a source electrode and a drain electrode of the second transistor are coupled; and
a source electrode of the reset transistor is coupled to the drain electrode of the second transistor.

14. The fingerprint information detection circuit of claim 11, wherein:

the feedback unit includes an inner plate, an outer plate, and a ground loop;
the inner plate and the outer plate form the first capacitor; and
the ground loop fully surrounds the inner and outer plates.

15. The fingerprint information detection circuit of claim 13, wherein:

the reset unit further includes second and third inverters;
an input of the second inverter is configured to receive a reset signal;
an output of the second inverter is coupled to an input of the third inverter; and
an output of the third inverter is coupled to the input of the first inverter.

16. A fingerprint information detection circuit, comprising:

an amplification unit;
a source follower unit;
a reset unit; and
a feedback unit, wherein:
the amplification unit is coupled to the source follower unit;
the reset unit is coupled to both the feedback unit and the amplification unit;
the feedback unit and the amplification unit are coupled;
the reset unit is configured to receive a reset signal;
the reset unit includes a reset transistor that is configured to store electric charges in response to a first state of the reset signal, and to inject stored electric charges into the feedback unit and the amplification unit in response to a second state of the reset signal that is opposite to the first state;
the reset unit further includes a second transistor that is configured to fully absorb electric charges that are generated by the reset transistor due to clock feedthrough when the reset signal is in the second state;
the feedback unit is configured to effectuate a change of capacitance when fingerprint information is detected; and
the feedback unit, the amplification unit, and the source follower unit are configured to output a voltage signal in relation to both the change of capacitance in the feedback unit and a portion of the stored electric charges in the reset transistor.

17. The fingerprint information detection circuit of claim 16, wherein:

the reset transistor is a NMOSFET;
the second transistor is another NMOSFET; and
a channel width of the reset transistor is twice a channel width of the second transistor.

18. The fingerprint information detection circuit of claim 17, wherein:

the reset unit further includes a first inverter whose input is coupled to a gate electrode of the reset transistor and whose output is coupled to a gate electrode of the second transistor;
a source electrode and a drain electrode of the second transistor are coupled; and
a source electrode of the reset transistor is coupled to the drain electrode of the second transistor.

19. The fingerprint information detection circuit of claim 16, wherein the feedback unit is grounded for discharging static electricity when touched by a finger.

20. The fingerprint information detection circuit of claim 16, wherein the amplification unit is configured to: receive a signal that comes only from the reset unit and the feedback unit, amplify the signal, and output the amplified signal to the source follower unit.

* * * * *